US009988663B2

(12) United States Patent
Miyashita et al.

(10) Patent No.: US 9,988,663 B2
(45) Date of Patent: Jun. 5, 2018

(54) METHOD FOR COLLECTING BIOLOGICAL MATERIAL AND DEVICE FOR COLLECTING BIOLOGICAL MATERIAL

(71) Applicant: HITACHI PLANT SERVICES CO., LTD., Tokyo (JP)

(72) Inventors: Noe Miyashita, Tokyo (JP); Shuichi Mori, Tokyo (JP); Yuta Nakatsuka, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days. days.

(21) Appl. No.: 14/434,214

(22) PCT Filed: Oct. 18, 2013

(86) PCT No.: PCT/JP2013/078333
§ 371 (c)(1),
(2) Date: Apr. 8, 2015

(87) PCT Pub. No.: WO2014/061785
PCT Pub. Date: Apr. 24, 2014

(65) Prior Publication Data
US 2015/0232908 A1    Aug. 20, 2015

(30) Foreign Application Priority Data
Oct. 19, 2012 (JP) .................................. 2012-231768

(51) Int. Cl.
*C12Q 1/06* (2006.01)
*C12M 1/00* (2006.01)
(Continued)

(52) U.S. Cl.
CPC .............. *C12Q 1/06* (2013.01); *C12M 33/00* (2013.01); *C12M 41/12* (2013.01); *C12M 47/04* (2013.01); *C12Q 1/008* (2013.01)

(58) Field of Classification Search
None
See application file for complete search history.

(56) References Cited

U.S. PATENT DOCUMENTS 6,238,857 B1    5/2001  Hattori et al.
6,254,834 B1    7/2001  Anderson et al.
(Continued)

FOREIGN PATENT DOCUMENTS

EP    0 299 078 A1    1/1989
EP    0 309 429 A2    3/1989
(Continued)

OTHER PUBLICATIONS

Aug. 4, 2015 Office Action issued in Japanese Patent Application No. 2012-231768.
(Continued)

*Primary Examiner* — P. Kathryn Wright
(74) *Attorney, Agent, or Firm* — Oliff PLC

(57) ABSTRACT

Provided is a device for collecting biological material from a microbe, the device including: a collection container that is used to collect a microbe from a liquid sample containing the microbe and to extract the biological material from the microbe; and a temperature control mechanism that controls a temperature of the collection container. Herein, the temperature control mechanism controls a temperature of the collection container so that the microbe is collected at a first temperature and the biological material is extracted from the microbe at a second temperature higher than the first temperature.

2 Claims, 4 Drawing Sheets

(51) Int. Cl.
*C12M 1/26* (2006.01)
*C12M 1/34* (2006.01)
*C12Q 1/00* (2006.01)

(56) References Cited

U.S. PATENT DOCUMENTS

| | | |
|---|---|---|
| 6,340,570 B1 | 1/2002 | Anderson et al. |
| 6,346,421 B1 | 2/2002 | Anderson et al. |
| 6,479,239 B1 | 11/2002 | Anderson et al. |
| 7,070,739 B1 | 7/2006 | Anderson et al. |
| 8,039,206 B1 | 10/2011 | Keenan |
| 2002/0127546 A1 | 9/2002 | Anderson et al. |
| 2002/0132230 A1 | 9/2002 | Anderson et al. |
| 2002/0132338 A1 | 9/2002 | Anderson et al. |
| 2002/0137026 A1 | 9/2002 | Anderson et al. |
| 2003/0138770 A1 | 7/2003 | Anderson et al. |
| 2005/0208608 A1* | 9/2005 | Raven .................. C12Q 1/485 435/8 |
| 2008/0241871 A1 | 10/2008 | Okanojo et al. |
| 2009/0054809 A1 | 2/2009 | Morishita et al. |
| 2009/0142785 A1 | 6/2009 | Osato et al. |
| 2010/0216183 A1 | 8/2010 | Okanojo et al. |
| 2011/0183371 A1* | 7/2011 | Noda .................. C12Q 1/008 435/39 |
| 2011/0315625 A1 | 12/2011 | Keenan et al. |

FOREIGN PATENT DOCUMENTS

| | | |
|---|---|---|
| EP | 1 574 564 A1 | 9/2005 |
| EP | 2 305 789 A1 | 4/2011 |
| JP | H02-286096 A | 11/1990 |
| JP | H05-030998 A | 2/1993 |
| JP | H05-184350 A | 7/1993 |
| JP | H07-135964 A | 5/1995 |
| JP | H09-107994 A | 4/1997 |
| JP | H11-155597 A | 6/1999 |
| JP | 2001-136999 A | 5/2001 |
| JP | 2002-505866 A | 2/2002 |
| JP | 2003-506073 A | 2/2003 |
| JP | 2004-313028 A | 11/2004 |
| JP | 2007-014239 A | 1/2007 |
| JP | 2008-249628 A | 10/2008 |
| JP | 2009-131186 A | 6/2009 |
| JP | 2010-193835 A | 9/2010 |
| WO | 2004/001022 A1 | 12/2003 |
| WO | 2006/109693 A1 | 10/2006 |
| WO | 2009/157510 A1 | 12/2009 |

OTHER PUBLICATIONS

Aug. 4, 2015 Decision of Dismiss the Amendment issued in Japanese Patent Application No. 2012-231768.
Partial Translation of Gotoda, et al. "Iyakuhin Mukin Seizo Shisetsu Ni Okeru Kankyo Biseibutsu Kensa, Atp-Ho O Mochiita Kuchu Fuyukin Sokutei Sochi No Kaihatsu." Clean Technology. vol. 21, No. 10, pp. 62-66, 2011.
Partial Translation of Noda, et al. "Bio Clean Room Shitsunai Kankyo No Jinsoku Kokando Biseibutsu Keisoku Gijutsu, Seibutsu Hakkoho O Riyo Shita Jido Seikin Keisoku Sochi" Clean Technology. vol. 19, No. 1, pp. 55-59, 2009.
Partial Translation of Kamitani, Matsuo, et al. "Development of Airborne Bacteria Measurement Device "Biomaytector"," Hitachi Plant Technology Giho. No. 5, pp. 52-55, 2011.
Apr. 8, 2014 Office Action issued in Japanese Application No. 2012-231768.
Gotoda, et al. "Iyakuhin Mukin Seizo Shisetsu Ni Okeru Kankyo Biseibutsu Kensa, Atp-Ho O Mochiita Kuchu Fuyukin Sokutei Sochi No Kaihatsu." Clean Technology. vol. 21, No. 10, pp. 62-66, 2011.
Kamitani, Matsuo, et al. "Development of Airborne Bacteria Measurement Device 'Biomaytector'." Hitachi Plant Technology Giho. No. 5, pp. 52-55, 2011.
Noda, et al. "Bio Clean Room Shitsunai Kankyo No Jinsoku Kokando Biseibutsu Keisoku Gijutsu, Seibutsu Hakkoho O Riyo Shita Jido Seikin Keisoku Sochi." Clean Technology. vol. 19, No. 1, pp. 55-59, 2009.
Jan. 14, 2014 International Search Report issued in Japanese Application No. PCT/JP2013/078333.
Jan. 14, 2014 Written Opinion issued in Japanese Application No. PCT/JP2013/078333.
Haiyan Wang et al., "Rapid and Economical Eetection of *Salmonella enteritidis* in Eggs by the Polymyxin-cloth Enzyme Immunoassay," International Journal of Food Microbiology vol. 24, No. 3, 1995, pp. 397-406.
May 9, 2016 Extended European Search Report issued in European Patent Application No. 13847140.4.
Mar. 9, 2017 Office Action issued in European Patent Application No. 13847140.4.

\* cited by examiner

METHOD FOR COLLECTING BIOLOGICAL MATERIAL AND DEVICE FOR COLLECTING BIOLOGICAL MATERIAL

BACKGROUND OF THE INVENTION

Technical Field

The present invention relates to a method for collecting cellular biological material contained in a sample, and a device for collecting biological material.

Background Art

Conventionally, a method (i.e., counting method) for quantifying microbes in a sample has been known as an ATP assay in which the number of microbes is indirectly counted by quantifying a microbe-derived ATP (adenosine triphosphate) as an index (see, for example, Patent Literatures 1 to 3). This ATP assay is a quantifying method including: having an ATP extraction reagent contact with microbes contained in a sample; extracting endogenous ATP from the microbes; and counting the number of the microbes in accordance with an amount of luminescence given when the ATP reacts with a luminescent reagent.

Meanwhile, the number of collected microbes may be counted by, for example, determining the number of colonies of the microbes cultured on plate agar. This counting method requires several days. By contrast, when the above ATP assay is used, the time from collection of microbes to their counting can be markedly shortened to about one to several hours.

CITATION LIST

Patent Literatures

Patent Literature 1: Japanese Unexamined Patent Publication No. H11-155597
Patent Literature 2: Japanese Unexamined Patent Publication No. 2008-249628
Patent Literature 3: Japanese Unexamined Patent Publication No. 2009-131186

SUMMARY OF THE INVENTION

Technical Problem

In a conventional ATP assay, a surfactant such as benzalkonium chloride has been used as an ATP extraction reagent. Use of such an ATP extraction reagent enables a microbial cell membrane to be disrupted, thereby extracting endogenous ATP from a microbe.

However, different species of microbe have different resistance against the ATP extraction reagent. Because of this, although an ATP extraction reagent may be effective in extracting ATP from, for example, a microbial species A, ATP may not be sufficiently extracted from a different microbial species B.

Accordingly, when the conventional ATP assay is used as a method for quantifying microbes, an ATP yield therein varies depending on a microbial species. Thus, microbes may not be quantified with high sensitivity and precision. Under the above situation, demanded is a method for collecting a biological material from microbes, by which a sufficient amount of the biological material can be collected regardless of a species of the microbes when the biological material such as ATP is collected from those microbes.

From this viewpoint, it is an object of the present invention to provide a method and a device for collecting biological material, the method and device enabling a sufficient amount of the biological material to be collected from microbes regardless of a species of the microbes.

Solution to Problem

In order to solve the above problem, an aspect of the present invention provides a method for collecting biological material from a microbe, the method including: a collection step of collecting a microbe from a medium containing the microbe at a first temperature; a temperature raising step of heating the microbe collected during the collection step to a second temperature higher than the first temperature; and an extraction step of extracting the biological material from the microbe at the second temperature.

Further, in order to solve the above problem, another aspect of the present invention provides a device for collecting biological material from a microbe, the device including: a collection container that is used to collect a microbe from a medium containing the microbe and to extract a biological material from the microbe; and a temperature control mechanism that controls a temperature of the collection container. Herein, the temperature control mechanism controls the temperature of the collection container so that the microbe is collected at a first temperature and the biological material is extracted from the microbe at a second temperature higher than the first temperature.

Advantageous Effects of the Invention

The present invention provides a method and a device for collecting biological material, the method and device enabling collection of a sufficient amount of the biological material from microbes regardless of a species of the microbes.

EMBODIMENTS FOR CARRYING OUT THE INVENTION

Next, embodiments of the present invention will be described in detail by appropriately referring to the attached drawings.

A method and a device for collecting biological material according to embodiments of the present invention are characterized in that: a microbe is collected from a microbe-containing medium at a predetermined first temperature; and ATP (adenosine triphosphate) that is a biological material of the collected microbe is extracted and collected from the microbe at a second temperature higher than the first temperature.

Hereinafter, an entire construction of a device for collecting biological material according to an embodiment of the present invention will be described in detail. Then, while explaining operation of the device for collecting biological material, a method for collecting biological material and a principle of quantifying the collected biological material will be further described.

<Device for Collecting Biological Material>

Figure 1:
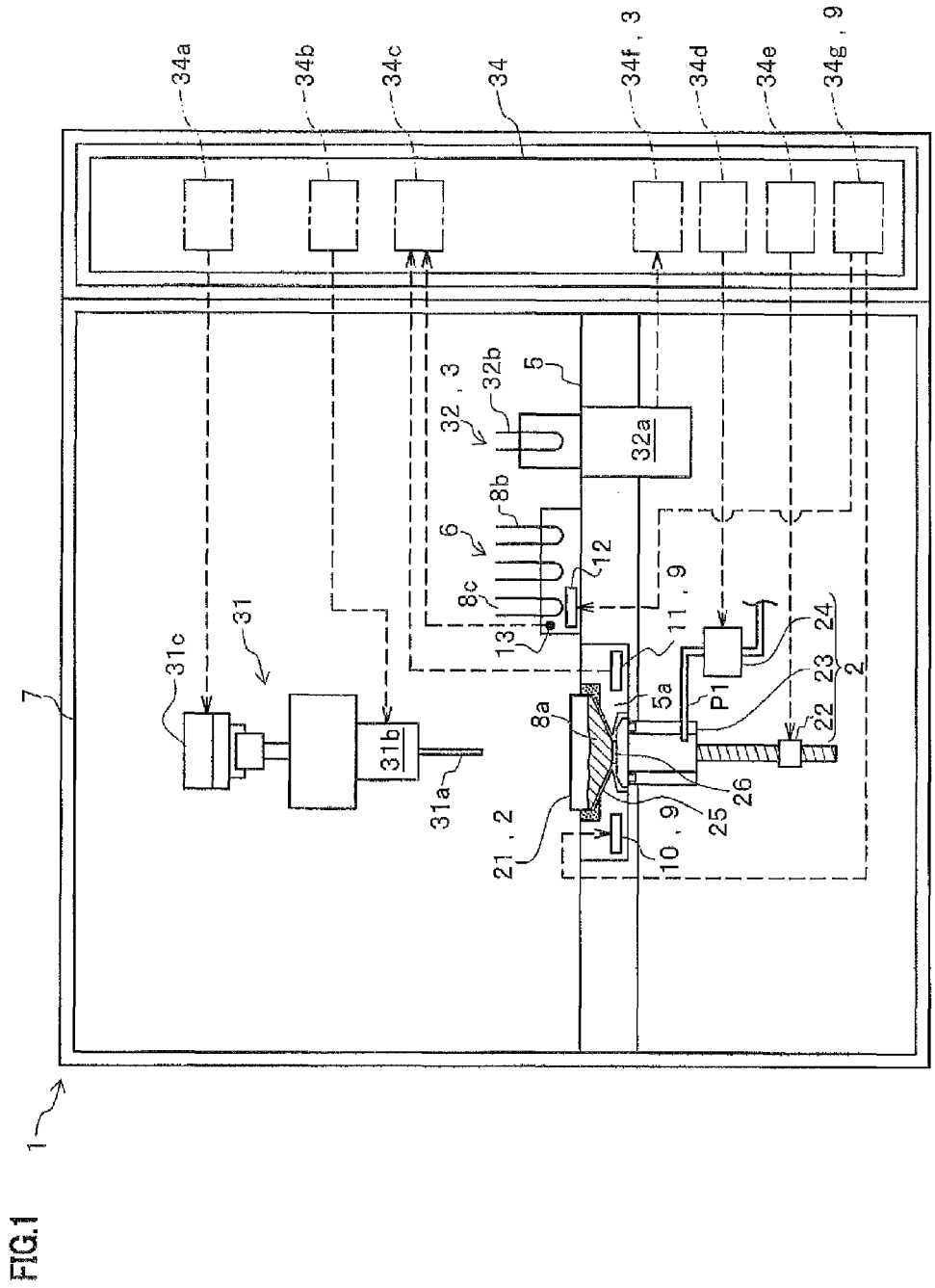
FIG. 1 illustrates a construction of a device for collecting biological material according to an embodiment of the present invention.

FIG. 1 shows a device 1 for collecting a biological material. The device 1 includes: a collection container 21 that is used to collect a microbe from a liquid sample 8a containing the microbe (not shown) and to extract biological material ATP from the microbe; and a temperature control mechanism 9 that controls a temperature of the collection container 21. Note that a term of "liquid sample 8a containing the microbe" corresponds to a term of "medium containing the microbe" set forth in the attached "Claims".

(Collection Container)

The collection container 21 includes: a funnel-shaped main body 25; and a filter 26 arranged at a bottom of the container 21.

This collection container 21 is used to collect a microbe on the filter 26 while a suction head 23 of the filtration unit 2 described below sucks the liquid sample 8a in the collection container 21. Then, the liquid dispensing unit 31 dispenses an ATP extraction reagent in the container 21. In this way, a biological material is extracted and collected from the microbe. Note that a term of "liquid dispensing unit 31" corresponds to a term of "dispensing mechanism" set forth in the attached "Claims".

The filter 26 according to the present embodiment is formed in a stack of two layers composing of a hydrophilic filter 26a (see FIG. 5A) and a hydrophobic filter 26b (see FIG. 5A) as described below. Although the structure is not shown in FIG. 1, the hydrophilic filter 26a is disposed at an upper side and the hydrophobic filter 26b is disposed at a lower side of the stack of the two layers.

The filter 26 retains the liquid sample 8a that has been injected into the main body 25 on the filter 26 unless the liquid sample 8a is sucked via the suction head 23. In addition, when the liquid sample 8a is sucked via the suction head 23, the microbe (not shown) is retained on the filter 26 and the liquid components are discharged through the filter 26 to the suction head 23 side.

Herein, the collection container 21 is mounted on a predetermined position of a treatment stage 5 included in the device 1 for collecting biological material. In the present embodiment, the collection container 21 is detachably mounted on a mounting section 5a for a collection container, the mounting section 5a being arranged in the treatment stage 5. Note that the mounting section 5a for a collection container according to the present embodiment is made of a material with efficient heat conductivity such as an aluminum alloy.

(Filtration Unit)

The filtration unit 2 includes: the collection container 21; the suction head 23; a lift mechanism 22 that moves the suction head 23 up and down; and a suction pump 24 that sucks contents of the collection container 21 through the suction head 23.

As described above, the suction head 23 is vertically movable up and down via the lift mechanism 22. When contents in the collection container 21 are filtered through the filter 26, the lift mechanism 22 lifts the suction head 23 so that the suction head 23 is connected with the collection container 21. Further, when the collection container 21 is mounted on the treatment stage 5 or removed from the treatment stage 5, the lift mechanism 22 moves down the suction head 23 to disconnect the suction head 23 from the collection container 21.

The suction pump 24 is arranged in the middle of a pipe P1 that extends from the suction head 23. When the suction pump 24 is actuated, the liquid components contained in the collection container 21, as described above, pass through the filter 26, the suction head 23, and the suction pump 24 to be discharged into a waste tank (not shown) of the device 1 for collecting biological material.

Herein, a suction pump controller 34d and a lift mechanism controller 34e of a control unit 34 control actuation and stop of the suction pump 24 and the lift mechanism 22, respectively.

(Liquid Dispensing Unit)

A liquid dispensing unit 31 includes: a liquid dispensing nozzle 31a; a dispensing pump 31b that sucks a predetermined amount of liquid from the liquid dispensing nozzle 31a or discharges that thereto; an actuator 31c that three-dimensionally moves the liquid dispensing nozzle 31a in a housing 7 of the device 1 for collecting biological material; and an actuator controller 34a and a flow rate controller 34b of the control unit 34.

The liquid dispensing nozzle 31a of this liquid dispensing unit 31 is used in a step of measuring an intensity of ATP luminescence as described below. A predetermined amount of an ATP extract 8d (see FIG. 4C) as obtained from the collection container 21 is transferred to a tube 32b for luminescence assay performed by an emission intensity-measuring unit 32 included in an ATP-quantification mechanism 3. In addition, the liquid dispensing nozzle 31a transfers an ATP luminescent reagent 8b placed in a reagent holder 6 to the tube 32b for luminescence assay.

The actuator controller 34a controls actuator 31c in a predetermined manner so that the liquid dispensing nozzle 31a moves three-dimensionally. Further, the flow rate controller 34b controls the dispensing pump 31b in a predetermined manner so that dispensed amounts of the ATP luminescent reagent 8b and the ATP extract 8d etc. (see FIG. 4C) are adjusted respectively.

(Temperature Control Mechanism)

A temperature control mechanism 9 has a plurality of components and includes: a first heating unit 10 such as a heater that heats the collection container 21; a first temperature sensor 11 that detects a temperature of the collection container 21 and outputs a temperature detection signal on this temperature; and a temperature controller 34g that controls a calorific value of the first heating unit 10 based on the temperature detection signal outputted from the first temperature sensor 11.

The first heating unit 10 and the first temperature sensor 11 are arranged adjacently to the collection container 21 on the mounting section 5a for a collection container. This arrangement allows a temperature of the collection container 21 to be accurately controlled.

The temperature controller 34g of the control unit 34 outputs instructions to a given inverter or the like to supply power to the first heating unit 10 so that the first heating unit 10 arranged on the mounting section 5a for a collection container generates heat. More specifically, the temperature controller 34g controls the first heating unit 10 to heat the liquid sample 8a in the collection container 21 to the first temperature and keep the temperature at the first temperature. At this time, the temperature controller 34g of the control unit 34 turns on and off the first heating unit 10 based on temperature detection signals outputted from the first temperature sensor 11 arranged on the mounting section 5a for a collection container and inputted through an input section 34c for temperature detection signals. This operation allows a temperature of the liquid sample 8a in the collection container 21 to be controlled and kept within the above temperature range.

The input section 34c of the control unit 34 includes an interface and an A/D converter, and receives temperature detection signals outputted from the first temperature sensor 11. The temperature controller 34g includes a central processing unit (not shown) and a storage unit (not shown). Those units are configured to cooperate together based on the temperature detection signals inputted through the input section 34c for temperature detection signals, whereby the first heating unit 10 is turned on and off as described above.

Note that timing of controlling a calorific value generated by the first heating unit 10 will be described in detail hereinafter (see FIG. 3).

As described below, this temperature controller 34g is configured to control a calorific value in a second heating unit 12 such as a heater that raises a temperature of an ATP extraction reagent 8c placed in the reagent holder 6.

Note that a term of "ATP extraction reagent 8c" corresponds to a term of "biological material extraction reagent" set forth in the attached "Claims".

The temperature controller 34g makes the second heating unit 12 turned on and off based on temperature detection signals outputted from a second temperature sensor 13 arranged in the reagent holder 6 in the vicinity of the ATP extraction reagent 8c and inputted through the input section 34c for temperature detection signals. This operation allows the temperature of the ATP extraction reagent 8c in the reagent holder 6 to be controlled and kept within the predetermined temperature range as described hereinafter.

Note that the "mechanism for raising a temperature of an extraction reagent" set forth in the attached "Claims" includes the second heating unit 12, the second temperature sensor 13, and the temperature controller 34g.

(ATP Quantification Mechanism)

The device 1 for collecting biological material of the present embodiment includes an ATP (i.e., biological material) quantification mechanism 3 in addition to the collection container 21, the filtration unit 2, the liquid dispensing unit 31, and the temperature control mechanism 9.

The ATP quantification mechanism 3 primarily includes: the emission intensity-measuring unit 32; and an arithmetic part 34f of the control unit 34. The arithmetic part 34f determines quantity of ATP contained in a microbe based on detection signals indicating an ATP luminescence intensity, outputted from the emission intensity-measuring unit 32.

As described below in detail, the emission intensity-measuring unit 32 includes: a tube 32b for luminescence assay and a main body 32a for light detection. Herein, the tube 32b receives a dispensed ATP extract and an ATP luminescent reagent 8b to cause a luminescent reaction. The main body 32a has a photo multiplier or the like detecting the ATP luminescence intensity during the luminescent reaction.

The main body 32a for light detection outputs detection signals indicating the ATP luminescence intensity via the tube 32b to the arithmetic part 34f of the control unit 34. That is, the main body 32a for light detection outputs detection signals which include the "ATP luminescence intensity reflecting an ATP amount in an ATP extract".

The arithmetic part 34f calculates an ATP amount contained in microbes of the liquid sample 8a based on the detection signals including the "ATP luminescence intensity reflecting an ATP amount in the ATP extract". Herein, the detection signals are outputted from the main body 32a for light detection. Note that algorithm for calculating an ATP amount by the arithmetic part 34f will be described in detail hereinafter.

<Operation of Device for Collecting Biological Material>

Figure 2:
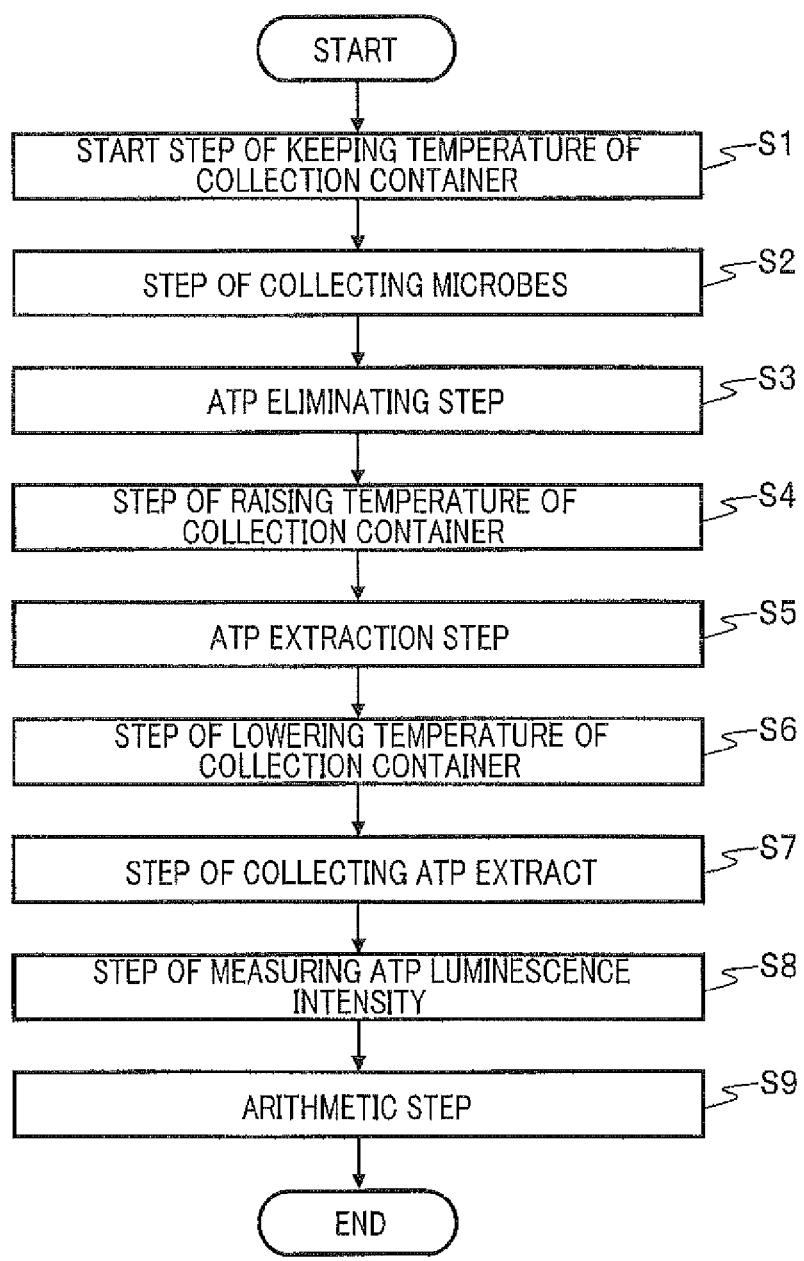
FIG. 2 is a flow chart outlining a method for collecting biological material according to an embodiment of the present invention.

Next, a method for collecting biological material will be described while explaining operation of the device 1 for collecting biological material. In addition, a principle of quantifying a biological material thus collected will be also described. Here, the collecting method and qualifying principle will be described referring to FIGS. 1 and 2. FIG. 2 is a flow chart outlining a method for collecting biological material according to an embodiment of the present invention.

First, in the device 1 for collecting biological material as shown in FIG. 1, the collection container 21 is placed on the mounting section 5a of the treatment stage 5. Next, the liquid sample 8a to be a detection target is injected into the collection container 21. Then, a start switch (not shown) is turned on to make the control unit 34 execute the following procedure.

The temperature controller 34g of the control unit 34 starts a step of keeping a temperature of a collection container so as to maintain a temperature of the collection container 21 at the first temperature (Step S1 in FIG. 2). Specifically, the temperature controller 34g controls a calorific value of the first heating unit 10 so that the temperature of the collection container 21 is set to be the first temperature that is higher than the room temperature and lower than the second temperature described below, based on the temperature detection signals outputted from the first temperature sensor 11.

Note that the "first temperature" of the present embodiment is not particularly limited as long as the first temperature is higher than room temperature and less than the second temperature described below. The temperature of contents of the collection container 21, however, is desirably set to be within a range (e.g., 30° C.) from higher than room temperature to lower than 40° C.

Next, the lift mechanism controller 34e of the control unit 34 outputs instructions to the lift mechanism 22 to move the suction head 23 up and connect the suction head 23 with the collection container 21.

Further, the suction pump controller 34d of the control unit 34 actuates the suction pump 24. Then, through the suction head 23, filtration of the contents (i.e., liquid sample 8a) in the collection container 21 is started. This allows microbes to be collected on the filter 26 (Step S2 in FIG. 2).

At this time, the liquid components in the liquid sample 8a are discharged toward the suction head 23. Most of extracellular ATP present outside the microbial cells, included in liquid components of the liquid sample 8a, is discharged together with the liquid components.

In next Step S3, an ATP eliminating reagent is dispensed in the collection container 21 to eliminate what is called free ATP present outside the microbial cells. Herein, the ATP eliminating reagent is placed in the reagent holder 6. Then, the liquid dispensing nozzle 31a of the liquid dispensing unit 31 is used to dispense the ATP eliminating reagent from the reagent holder 6 into the collection container 21. Dispensing the ATP eliminating reagent completely eliminates the free ATP.

Examples of this ATP eliminating reagent include an ATPase.

Next, the temperature controller 34g of the control unit 34 starts a step of raising a temperature of the collection container 21 (Step S4 in FIG. 2). Specifically, the temperature controller 34g controls a calorific value of the first heating unit 10 so that the temperature of the collection container 21 is set to be the predetermined second temperature, based on the temperature detection signals outputted from the first temperature sensor 11.

Note that in terms of the "second temperature" of the present embodiment, the temperature of contents of the collection container 21 is desirably set to be within a range from higher than 40° C. to lower than 100° C., for example, at 60° C.

Next, while the second temperature is maintained, an ATP extraction step of extracting ATP from the microbes in the collection container 21 is carried out (Step S5 in FIG. 2).

Specifically, when the input section for temperature detection signals 34c determines that the temperature of the collection container 21 reaches the second temperature, based on temperature detection signals outputted from the first temperature sensor 11, the actuator controller 34a and the flow rate controller 34b control the actuator 31c and the dispensing pump 31b, respectively, so that the liquid dispensing nozzle 31a dispenses a predetermined amount of the ATP extraction reagent 8c into the collection container 21.

Figure 4A:
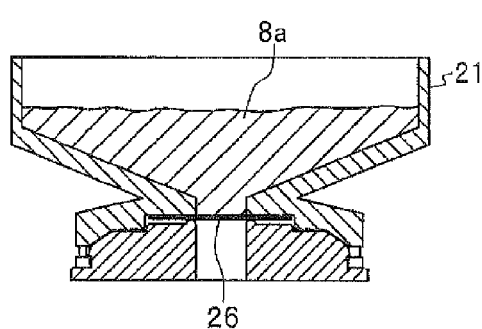
FIGS. 4A to 4C are cross-sectional views of a collection container in which a level of liquid is indicated when a method for collecting biological material according to an embodiment of the present invention is carried out.
Figure 4B:
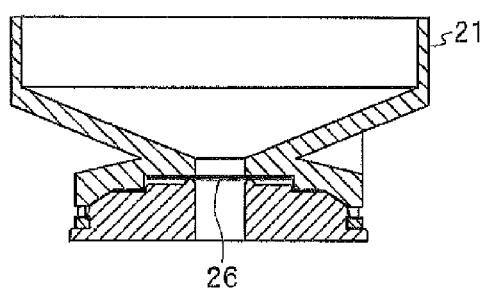
Figure 4C:
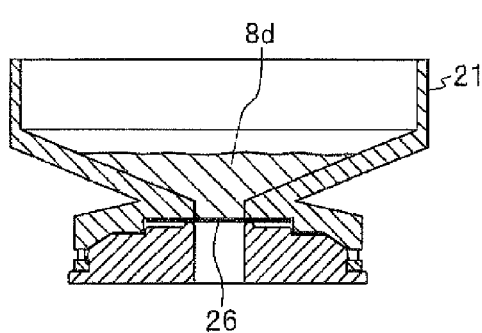

Dispensing this ATP extraction reagent 8c makes it possible to extract ATP contained in microbes and produce the ATP extract 8d in the collection container 21 (see FIG. 4C). Here, the ATP eliminating reagent dispensed in the collection container 21 during Step S4 is inactivated when the ATP eliminating reagent contacts with the ATP extraction reagent 8c.

Examples of the ATP extraction reagent 8c suitably used include a surfactant, a mixed solution of ethanol and ammonia, methanol, ethanol, trichloroacetic acid, perchloric acid, and a Tris buffer. Among them, preferred is a surfactant. Examples of the surfactant include sodium dodecyl sulfate, potassium lauryl sulfate, sodium monolauroyl phosphate, sodium alkylbenzene sulfonate, benzalkonium chloride, benzethonium chloride, cetylpyridinium chloride, cetyl trimethyl ammonium bromide, and myristyl dimethyl benzyl ammonium chloride.

Next, a step of lowering a temperature of the collection container 21 is carried out (Step S6 in FIG. 2). Specifically, the temperature controller 34g turns off the first heating unit 10 at the predetermined timing described hereinafter. By doing so, the temperature of the collection container 21 is dropped due to heat dissipation.

The temperature immediately after this temperature lowering step is not particularly limited, but may be room temperature or higher. In the present embodiment, however, it is assumed that the temperature lowering step is carried out so that the above temperature becomes equal to the first temperature.

After the temperature lowering step, the temperature controller 34g controls the temperature of the collection container 21 so as to keep it constant. Specifically, the temperature controller 34g of the present embodiment controls a calorific value of the first heating unit 10 so that the temperature of the collection container 21 is set to be the predetermined first temperature, based on the temperature detection signals outputted from the first temperature sensor 11.

Next, when the control unit 34 determines that the temperature of the collection container 21 is dropped to the first temperature, based on the temperature detection signals outputted from the first temperature sensor 11, the actuator controller 34a and the flow rate controller 34b control the liquid dispensing nozzle 31a to collect a predetermined amount of the ATP extract 8d (see FIG. 4C) in the collection container 21 (Step S7 in FIG. 2). Then, the liquid dispensing nozzle 31a transfers the ATP extract 8d thus collected to the tube 32b for luminescence assay.

Next, the actuator controller 34a and the flow rate controller 34b control the liquid dispensing nozzle 31a to dispense into the tube 32b the ATP luminescent reagent 8b placed in the reagent holder 6.

Examples of the ATP luminescent reagent 8b include a luciferase-luciferin reagent.

Accordingly, in the tube 32b for luminescence assay, ATP in the ATP extract reacts with the ATP luminescent reagent 8b to emit light.

Next, the arithmetic part 34f of the control unit 34 performs digital processing of detection signals outputted from the main body 32a for light detection after the main body 32a (see FIG. 1) detects an ATP luminescence intensity. The main body 32a measures the luminescence intensity based on a single photon counting method (Step S8 in FIG. 2).

Then, based on a standard curve defining a relationship between a pre-stored ATP amount (amol) and a luminescence intensity (CPS), the control unit 34 calculates an ATP amount (amol) corresponding to the luminescence intensity thus measured as described above. In this way, ATP in the liquid sample 8a (or medium) is quantified (Step S9 in FIG. 2). Execution of the Step S9 leads to completion of a biological material quantification step including a series of steps of a method for collecting biological material of the present embodiment.

Next, a relationship between a temperature change of the collection container 21 and a time course for a series of steps of a method for collecting biological material of the present embodiment will be described. FIG. 3, which will be described below, is a time chart outlining a method for collecting biological material of an embodiment of the present invention. Note that in FIG. 3, the ordinate represents a temperature T [° C.] of the collection container 21 and the abscissa represents a time point t [min].

Figure 3:
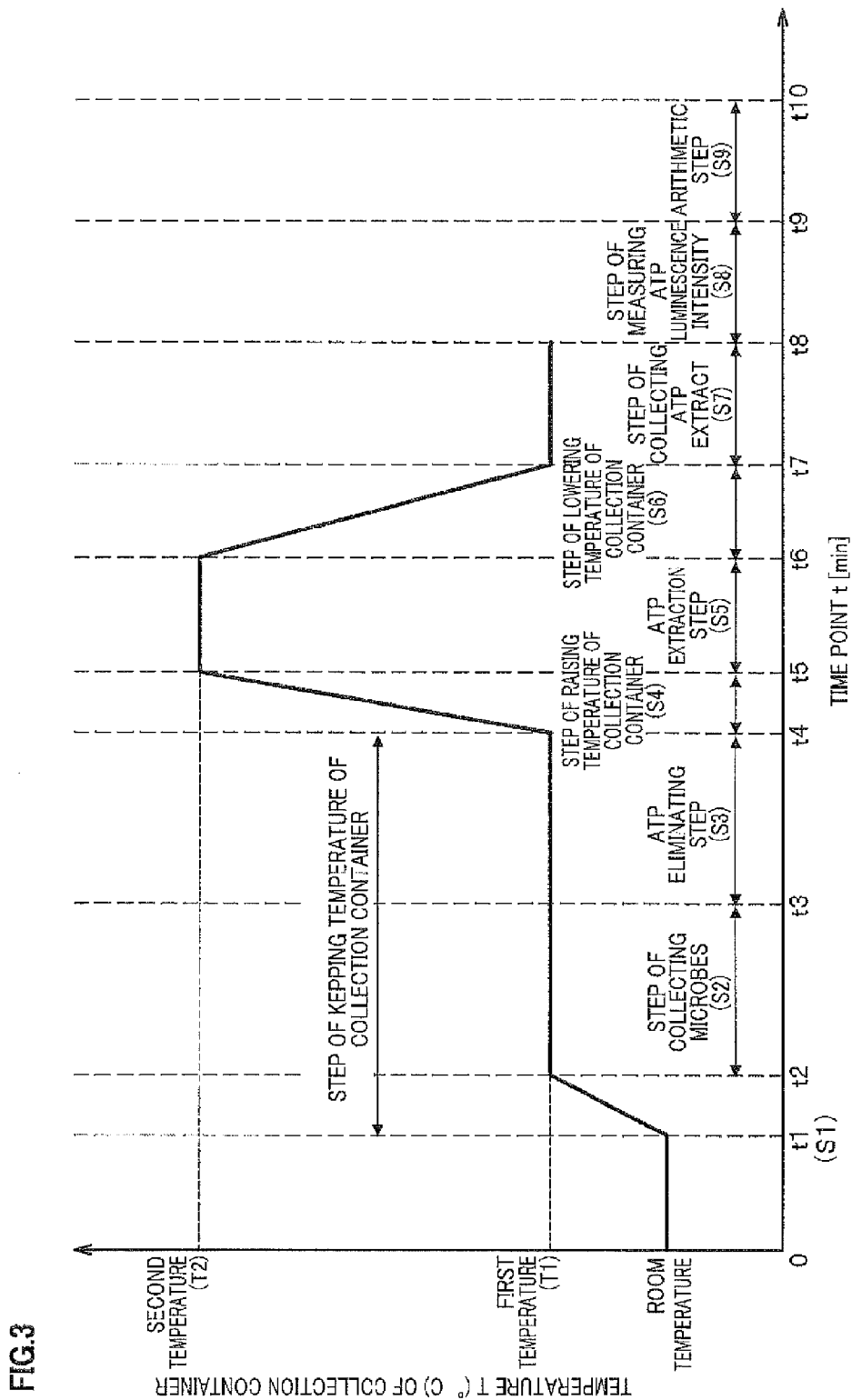
FIG. 3 is a time chart outlining a method for collecting biological material according to an embodiment of the present invention.

As shown in FIG. 3, the method for collecting biological material of the present embodiment include: a "step of keeping a temperature of a collection container" (Step S1 in FIG. 2), beginning at t1 [min]; a "step of collecting microbes" (Step S2 in FIG. 2) from t2 [min] to t3 [min]; a "ATP eliminating step" (Step S3 in FIG. 2) from t3 [min] to t4 [min]; a "step of raising a temperature of the collection container" (Step S4 in FIG. 2) from t4 [min] to t5 [min]; an "ATP extraction step" (Step S5 in FIG. 2) from t5 [min] to t6 [min]; a "step of lowering a temperature of the collection container" (Step S6 in FIG. 2) from t6 [min] to t7 [min]; and a "step of collecting ATP extract" (Step S7 in FIG. 2) from t7 [min] to t8 [min].

For reference, FIG. 3 shows additional steps after the "step of collecting ATP extract" (Step S7 in FIG. 2). Those steps include: a "step of measuring an ATP luminescence intensity" (Step S8 in FIG. 2) from t8 [min] to t9 [min]; and an "arithmetic step" (Step S9 in FIG. 2) from t9 [min] to t10 [min].

As illustrated in FIG. 3, the first heating unit 10 (see FIG. 1) is being turned off during the period from time 0 [min] to t1 [min]. Accordingly, the temperature of the collection container 21 is kept at room temperature. The collection container 21 is mounted on the treatment stage 5 during this period, and the collection container 21 is to be filled with the liquid sample 8a of examination target.

Next, as described above, the "step of keeping a temperature of a collection container" (Step S1 in FIG. 2) is started at t1 [min]. When the temperature of the collection container 21 reaches the first temperature (T1) at t2 [min], the temperature control mechanism 9 maintains the temperature of the collection container 21 at the first temperature (T1). This procedure also keeps the temperature of contents of the collection container 21 equal to the first temperature (T1).

Then, the microbe-containing liquid sample 8a (see FIG. 1) is filtered by the filtration unit 2 at the first temperature. This allows microbes to be separated and collected on the filter 26 (Step S2 in FIG. 2).

Next, the ATP eliminating step (Step S3 in FIG. 2) is started at the timing of t3 [min] when the filtration of the liquid sample 8a is ended. Here, the timing of t3 [min] can be determined by monitoring, for example, a change in pressure inside the suction head 23. In addition, the timing of t3 [min] may be set based on a filtration period [i.e., difference (t3–t2)] [min] that has been calculated beforehand via a simulation test. Alternatively, a liquid level of contents of the collection container 21 may be measured with, for example, an optical liquid level meter (not shown) to set the timing of t3 [min] when the contents of the collection container 21 become empty.

Such an ATP eliminating step is carried out at the first temperature (T1) by dispensing the ATP eliminating reagent in the collection container 21 as described above. Herein, it should be noted that an amount of the ATP eliminating reagent dispensed in the collection container 21 is extremely small in the present embodiment, and the collection container 21 is heated using the first heating unit 10. Accordingly, the first temperature (T1) hardly fluctuates when the ATP eliminating reagent is dispensed. However, note that when a relatively large amount of the ATP eliminating reagent is used, the temperature of the ATP eliminating reagent should be raised beforehand to about the same temperature as the first temperature (T1).

Such an endpoint t4 of the ATP eliminating step may be set based on an ATP eliminating period [i.e., difference (t4–t3)] [min] that has been calculated beforehand via a simulation test. Here, the stating time t3 [min] of the ATP eliminating step is a time when the liquid dispensing nozzle 31a starts to move from the initial position (or home position) toward the reagent holder 6. Thus, the ATP eliminating period [i.e., difference (t4–t3)] [min] as calculated via the simulation test includes a period from the initial movement of the liquid dispensing nozzle 31a until the dispensation of the ATP eliminating reagent into the collection container 21.

Next, the "step of raising a temperature of the collection container" (Step S4 in FIG. 2) is started at t4 [min] as described above. Then, the temperature of the collection container 21 reaches the second temperature (T2) at t5 [min]. After that, the temperature control mechanism 9 maintains the temperature of the collection container 21 at the second temperature (T2). This procedure also keeps the temperature of contents of the collection container 21 equal to the second temperature (T2).

Subsequently, the ATP extraction reagent 8c is dispensed to the microbes at the second temperature (T2) collected on the filter 26. Herein, extracellular free ATP is eliminated from the microbes. At this time, the dispensed ATP extraction reagent 8c has been heated with the second heating unit 12 that is the "temperature raising mechanism for extraction reagent". Because of this, the second temperature (T2) is maintained in the collection container 21 when the ATP extraction reagent 8c is dispensed in the collection container 21.

The endpoint t6 of the ATP extraction step may be set based on an ATP extraction period [i.e., difference (t6–t5)] [min] that has been calculated beforehand via a simulation test. In this connection, the staring time t5 [min] of the ATP extraction step is a time when the liquid dispensing nozzle 31a starts to move from the initial position (or home position) toward the reagent holder 6. Thus, the ATP extraction period [i.e., difference (t6–t5)] [min] as calculated via the simulation test includes a period from the initial movement of the liquid dispensing nozzle 31a until the dispensation of the ATP extraction reagent into the collection container 21.

Next, the "step of lowering a temperature of the collection container" (Step S6 in FIG. 2) is started at t6 [min] as described above. Then, the temperature of the collection container 21 reaches the first temperature (T1) at t7 [min]. After that, the temperature control mechanism 9 maintains the temperature of the collection container 21 at the first temperature (T1). This procedure also keeps the temperature of contents of the collection container 21 equal to the first temperature (T1).

In the above Step S5 of the ATP extraction step, the ATP extract 8d (see FIG. 4C) is prepared in the collection container 21. This ATP extract 8d is collected via the liquid dispensing unit 31, and is dispensed into the tube 32b (see FIG. 1) for luminescence assay while maintaining the first temperature (Step S7 in FIG. 2). Then, execution of the Step S7 leads to completion of a series of steps of a method for collecting biological material of the present embodiment. After those steps, the step of measuring an ATP luminescence intensity (Step S8 in FIG. 2) and the arithmetic step (Step S9 in FIG. 2) will be carried out.

Hereinafter, will be described advantageous effects exerted by the device 1 for collecting biological material and the method for collecting biological material of the present embodiment. FIGS. 4A to 4C are cross-sectional views of a collection container in which a level of liquid is indicated when a method for collecting biological material in an embodiment of the present invention is carried out. Further, FIGS. 5A to 5C are schematic magnified views showing the vicinity of a filter corresponding to FIGS. 4A to 4C, respectively.

Figure 5A:
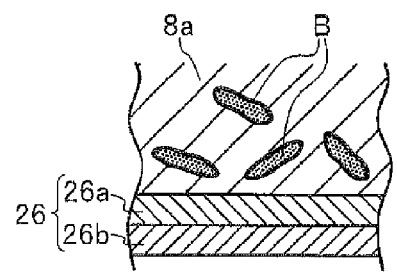
FIGS. 5A to 5C are magnified schematic views in the vicinity of a filter corresponding to FIGS. 4A to 4C.
Figure 5B:
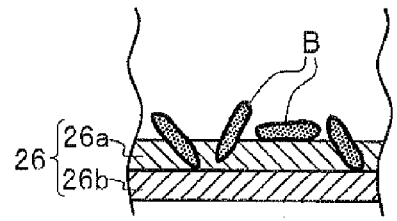
Figure 5C:
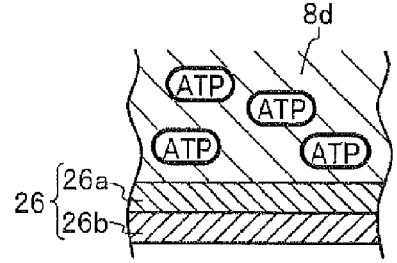

Note that in FIGS. 5A to 5C, an actual size of the microbes denoted by reference sign B is in a micrometer order. An actual size of ATP is at a molecular level. In this regards, FIGS. 5A to 5C do not show the microbes and ATP in relatively corrected sizes reflecting the actual sizes.

Immediately before the initiation of the step of collecting microbes (Step S2 in FIG. 2), as shown in FIG. 4A, the collection container 21 is filled with a predetermined amount (e.g., the amount in the present embodiment is 10 mL but is not limited thereto) of the liquid sample 8a. Note that in FIG. 4A, reference sign 26 denotes a filter.

As shown in FIG. 5A, the liquid sample 8a placed over the filter 26 contains microbes B. Note that in FIG. 5A, reference sign 26a denotes a hydrophilic filter and reference sign 26b denotes a hydrophobic filter as described hereinbefore.

When the microbes are collected on the filter 26 after the filtration in Step S2 (see FIG. 2), the inside of the collection container 21 becomes visually empty as shown in FIG. 4B. Here, as shown in FIG. 5B, the microbes are filtered out on the filter 26 (i.e., 26a and 26b).

After this Step S2, the "ATP eliminating step" (not shown) (Step S3, in FIG. 2) and the "step of raising a temperature of the collection container" (Step S4 in FIG. 2) are carried out. Then, as shown in FIG. 4C, the ATP extraction reagent 8c (see FIG. 1) is dispensed in the collection container 21 to extract ATP from the microbes B (FIG. 5B) (Step S5 in FIG. 2). At this time, an amount of liquid in the collection container 21 increases depending on a dispended amount of the ATP extraction reagent 8c as shown in FIG. 4C.

Herein, it should be noted that an actually dispensed amount of the ATP extraction reagent 8c is very small. However, for illustration convenience, the amount of liquid in FIG. 4C is exaggeratedly shown.

As shown in FIG. 5C, the ATP extract 8d containing ATP extracted from the microbes (i.e., living cells) is prepared in the collection container 21. In this connection, the ATP eliminating reagent that is an enzyme-based reagent is inactivated when contacting the surfactant-based ATP extraction reagent 8c (see FIG. 1). Because of this, the ATP eliminating reagent used in Step S3 hardly influences the measurement of the ATP luminescence intensity in Step S8 (see FIG. 2).

According to the device 1 for collecting biological material and method for collecting biological material according of the present embodiment, the ATP extraction step (Step S5 in FIG. 2) is carried out at an predetermined raised temperature (i.e., second temperature). Thus, regardless of a species of the microbe B (see FIG. 4A) contained in the liquid sample 8a (see FIG. 4A), the raised temperature decreases the microbe B's resistance against the ATP extraction reagent 8c (see FIG. 1).

This makes it easier to disrupt the cell membrane of the microbe B by the ATP extraction reagent 8c. Accordingly, the device 1 for collecting biological material and the method for collecting biological material of the present embodiment more increase extraction efficiency of ATP from the microbe B than a conventional device and method.

Therefore, a quantification method for biological material using the method for collecting biological material of the present embodiment quantifies ATP with higher accuracy and sensitivity than conventional methods.

Further, according to the device 1 for collecting biological material and the method for collecting biological material of the present embodiment, the microbes are collected (Step S2 in FIG. 2) from the liquid sample 8a (i.e., medium) at the first temperature which is lower than the second temperature and higher than room temperature. This makes it possible to suppress a decrease in bioactivity of the microbes B in the liquid sample 8a.

Because of this, an amount of ATP contained in the microbes B is maintained. Hence, a decease in an ATP recovery rate (or yield) can be prevented in the subsequent ATP extraction step (S5 in FIG. 2).

Therefore, a quantification method for biological material using the method for collecting biological material of the present embodiment quantifies ATP with higher accuracy and sensitivity than conventional methods.

Hereinbefore, embodiments of the present invention have been described in detail. However, the present invention is not limited to those embodiments, and various modifications can be carried out.

For example, in the above embodiment, when the step (Step S4 in FIG. 2) of raising a temperature of the collection container 21 is carried out, a calorific value generated by the first heating unit 10 is utilized for raising the temperature. However, in the present invention, the ATP extraction reagent 8c heated by the second heating unit 12 may be dispensed in the collection container 21. By doing so, the temperature of the microbes B (see FIG. 5B) is controlled (or kept) at the second temperature. Then, ATP is extracted from the microbes B at this second temperature. The above medication may be carried out.

Further, in the above embodiment, it is assumed that a heater, etc., is used as the first heating unit 10 and the second heating unit 12. By contrast, in the present invention, a Peltier element having an additional cooling function may be used instead of a heater. This makes it possible to shorten a time to reach a target temperature controlled by the control unit.

Moreover, in the above embodiment, the ATP luminescent reagent 8b may be dispensed to be mixed with the ATP extract 8d (see FIG. 4C) that has been dispensed in the tube 32b, so as to cause a luminescent reaction. By contrast, in the present invention, the ATP extract 8d may be dispensed to be mixed with the ATP luminescent reagent 8b that has been dispensed in the tube 32b so as to cause a luminescent reaction.

Examples of the microbes of the above embodiments include, but are not limited to, gram-positive bacteria (e.g., *Corynebacteria, Micrococcus, Staphylococcus aureus, Staphylococcus epidermidis, Bacillus cereus, Bacillus Subtilis*), gram-negative bacteria (e.g., *Citrobacter, Escherichia coli, Pseudomonas aeruginosa, Serratia*), and fungi (e.g., *Aspergillus oryzae, Penicillium notatum, Wallemia, Candida*).

Note that when the present invention is applied to spore-forming bacteria such as *Bacillus subtilis*, the above reagent may further include a cell conversion reagent using nutrients such as amino acids and/or saccharides.

Furthermore, in the above embodiments, ATP is assumed to be a biological material. However, the present invention is not limited to this, and biological materials such as DNA, RNA, or NAD extracted from the microbes B are applicable.

In addition, in the above embodiments, it is assumed to measure an intensity of luminescence emitted when a luminescent reagent for biological material reacts with a biological material. By contrast, in the present invention, a biological material may be quantified based on fluorescence generated when the biological material is irradiated with excitation light.

Further, when an endotoxin contained in a cell membrane of gram-negative bacteria is quantified as a biological material, Limulus Amebocyte Lysate may be used as a luminescent reagent for biological material.

In addition, in the above embodiments, it is assumed to use a liquid sample 8a as a "microbe-containing medium". Here, the "microbe-containing medium" may be a gel carrier. For example, after the gel carrier is used to capture microbes floating in the air, the gel carrier placed in the collection container 21 may be mixed with, for example, a buffer solution to prepare a liquid sample 8a.

Herein, examples of the gel carrier include a material that causes a phase transition from gel to sol by raising the temperature from room temperature. Such a material is preferably liquefied in a range from 30° C. to less than 40° C. Particularly, examples of a more preferable material include gelatin, a mixture of gelatin and glycerol, and a 10:1 copolymer of N-acryloyl glycinamide and N-methacryloyl-N'-biotinyl propylene diamine.

LIST OF REFERENCE SIGNS

1 Device for collecting biological material
2 Filtration unit

3 Quantification mechanism
5 Treatment stage
5a Mounting section for collection container
6 Reagent holder
7 Housing
8a Liquid sample (i.e., Medium)
8b ATP luminescent reagent
8c ATP extraction reagent (i.e., Biological material extraction reagent)
8d ATP extract
9 Temperature control mechanism
10 First heating unit
11 First temperature sensor
12 Second heating unit
13 Second temperature sensor
21 Collection container
22 Lift mechanism
23 Suction head
24 Suction pump
25 Main body
26 Filter
26a Hydrophilic filter
26b Hydrophobic filter
31 Liquid dispensing unit (i.e., Dispensing mechanism)
31a Liquid dispensing nozzle
31b Dispensing pump
31c Actuator
32 Emission intensity-measuring unit
32a Main body for light detection
32b Tube for luminescence assay
34 Control unit
34a Actuator controller
34b Flow rate controller
34c Input section for temperature detection signals
34d Suction pump controller
34e Lift mechanism controller
34f Arithmetic part
34g Temperature controller
P1 Pipe
B Microbe

The invention claimed is:

1. A device for collecting ATP from a microbe, comprising:
 a collection container that is used to collect a microbe from a medium containing the microbe and to extract the ATP from the microbe; and
 a temperature control mechanism comprising a heating unit configured to heat the collection container, a temperature sensor configured to detect a temperature of the collection container and output temperature detection signals based on the temperature of the collection container, and a temperature controller having control logic configured to:
  i) control the heating unit to heat the medium containing the microbe in the collection container to a predetermined first temperature set from 30° C. to less than 40° C. to collect the microbe from the medium at the first temperature while suppressing a decrease in bioactivity of the microbe based on the temperature detection signals outputted from the temperature sensor, and then keep the temperature at the first temperature to eliminate free ATP present outside the microbe based on the temperature detection signals outputted from the temperature sensor;
  ii) raise the temperature of the collection container to a predetermined second temperature that is higher than the first temperature to extract ATP from the microbe at the second temperature based on the temperature detection signals outputted from the temperature sensor; and
  iii) lower the temperature of the collection container back to the first temperature to collect a predetermined amount of ATP extract based on the temperature detection signals outputted from the temperature sensor.

2. The device for collecting ATP from a microbe according to claim 1, wherein the temperature controller has further control logic configured to maintain the temperature of the collection container at the first temperature for a predetermined time while the predetermined amount of ATP extract is collected based on the temperature detection signals outputted from the temperature sensor.

* * * * *